United States Patent [19]

Tokuyama et al.

[11] 4,414,255
[45] Nov. 8, 1983

[54] WATER ABSORBING SHEET ASSEMBLY

[75] Inventors: Mitsuru Tokuyama; Yoshimi Tsuchiya; Hikotaro Kawaguchi, all of Utsunomiya; Masayuki Sagae, Ichikaimachi; Kenji Ohki, Chiba, all of Japan

[73] Assignee: Kao Soap Co., Ltd., Tokyo, Japan

[21] Appl. No.: 141,742

[22] Filed: Apr. 18, 1980

[30] Foreign Application Priority Data

May 9, 1979 [JP] Japan ................................. 54-56562

[51] Int. Cl.³ .................... B32B 3/28; B32B 29/00
[52] U.S. Cl. .................................. 428/154; 156/209; 156/290; 162/113; 162/117; 162/205; 428/172; 428/198; 428/218; 428/327; 428/535

[58] Field of Search ............... 156/290, 209, 210, 219, 156/220, 582; 162/134, 113, 117, 205; 428/154, 198, 218, 156, 166, 172, 178, 183, 184, 212, 327, 535

[56] References Cited

U.S. PATENT DOCUMENTS

| | | | |
|---|---|---|---|
| 3,908,058 | 9/1975 | Russell et al. | 428/198 |
| 3,961,119 | 6/1976 | Thomas | 428/198 |
| 4,260,443 | 4/1981 | Lindsay et al. | 156/290 |
| 4,307,141 | 12/1981 | Walbrun | 428/154 |
| 4,320,162 | 3/1982 | Schulz | 428/154 |

*Primary Examiner*—Bruce H. Hess
*Attorney, Agent, or Firm*—Flynn, Thiel, Boutell & Tanis

[57] ABSTRACT

A water-absorbing sheet assembly comprises two sheets, at least one of which is a water-permeable sheet, and a polymeric absorbent inserted between said two sheets, wherein at least a part of said two sheets are pressed and bonded to each other.

5 Claims, 7 Drawing Figures

WATER ABSORBING SHEET ASSEMBLY

BACKGROUND OF THE INVENTION

1. FIELD OF THE INVENTION

The present invention relates to a water-absorbing sheet assembly having a novel structure.

2. DESCRIPTION OF PRIOR ARTS

As the absorbing material of a sanitary article, such as a sanitary napkin or a disposable diaper, there have heretofore been used pulp, cotton and crepe paper. Recently, researches have been made with a view to reducing the weight and volume in absorbing materials of these sanitary articles and as the result, polymeric absorbents have been developed.

SUMMARY OF THE INVENTION

We have made investigations on highly absorbing sheet materials formed by using these polymeric absorbents and found that good results can be obtained by a composite sheet assembly formed by inserting and interposing a polymeric absorbent between two sheets, at least one of which is a water-permeable sheet, and pressing and bonding at least parts of said two sheets to each other. Based on this finding, we have now completed the present invention.

Conventional crepe absorbing papers are conveniently used as the above-mentioned two sheets. Accordingly, the present invention will now be described with reference mainly to embodiments where these crepe absorbing papers are used. However, in the present invention, if one sheet is a water-permeable sheet, any other appropriate sheet can be used as the other sheet.

For the preparation of a water-absorbing sheet assembly of the present invention, a polymeric absorbent is interposed between two crepe absorbing papers, and the assembly is pressed and processed by an embossing roll to fix the sheets on the embossed and pressed areas and form a laminate composite structure. We made special investigations on the embossing pattern and the embossing manner, and found that by adopting an improved mechanism for forming a composite structure, a highly absorbing sheet assembly having much improved capacities can be obtained with great economical advantages.

Characteristics of constituent materials heretofore used for conventional highly absorbing sanitary sheet materials will now be described. In such conventional highly absorbing sanitary sheet material, a water-absorbing paper or non-woven fabric such as a rayon paper, which has a base weight of 10 to 40 g/m$^2$ and a crepe ratio of 10 to 40%, is used as an upper paper, and as a lower paper, there is used (1) the same paper as the upper paper, (2) a water-proof processed paper treated with a sizing agent to render the paper water-proof, (3) an impermeable sheet of polyethylene, polypropylene or the like, or (4) a sheet formed by laminating the sheet (3) on the paper (1) or (2). This sheet material has a good compatability with blood, urine, water or other liquid (hereinafter inclusively called "liquid") and it is creped. Accordingly, this sheet material is more bulky than orindary water-absorbing paper and is excellent in the liquid-retaining property, the water-absorbing property and the water-absorbing speed. However, the liquid-retaining property of this sheet material is still insufficient when it is used as an absorbent of a highly absorbing sanitary sheet material for which high capacities are required. As the polymeric absorbent, there are used starch polymers, acrylic acid type polymers and cellulose type polymers, and some of these polymeric absorbents can absorb the liquid in an amount 50 times the weight thereof. These polymeric absorbents are excellent in the liquid-retaining property. However, their compatibility with the liquid is poor and the water-absorbing speed is low.

Accordingly, in order to prepare a composite material without degrading or losing excellent properties of the constituent materials, it is indispensable that (1) the crepe ratio of the crepe paper should not be reduced and (2) the contact area between the polymeric absorbent and the liquid should be increased. We found that the embossing pattern and embossing area are important factors for satisfying both the requirements (1) and (2).

When a crepe paper is embossed, it is ordinarily stretched in the embossing direction and is elongated. Accordingly, in order to retain a high crepe ratio, it is preferred to minmize the embossing pressure. On the other hand, in order to retain a good dimension stability and shape-retaining property in a highly absorbing sanitary sheet material formed by bonding a polymeric absorbent to such crepe paper, a certain embossing pressure should be applied.

In view of the foregoing, it is preferred to adopt a high efficiency embossing method, that is, an embossing method in which a good dimension and shape stability can be imparted to the material while the requirements (1) and (2) are satisfied. We made researches with a view to developing such an embossing method. It was found that when an assembly comprising two sheets as mentioned above and a polymeric absorbent interposed therebetween is embossed by a pressing and bonding apparatus comprising an embossing roll having a surface comprising a great number of arranged convexities, a great number of arranged concavities and flat portions, and a receiving roll having a plain surface, thereby to press-bond parts to the two sheets to each other, a highly absorbing sanitary sheet material having an embossed pattern meeting the above-mentioned requirements can be obtained. In the composite sheet assembly according to the present invention, the press-bonded areas of the two sheets comprise relatively weakly press-bonded parts processed by the flat portions of the embossing roll and relatively strongly press-bonded parts processed by the convexities of the embossing roll. The portions of the sheets corresponding to the concavities on the surface of the embossing roll are formed into non-press-bonded areas. The sheet assembly according to the present invention will now be described with reference to the accompanying drawings.

Figure 1:
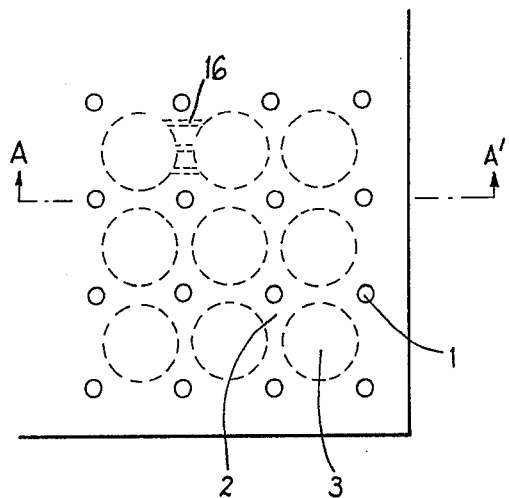
FIG. 1 is a plan view showing an embossing pattern suitable for practising the present invention.
Figure 2:
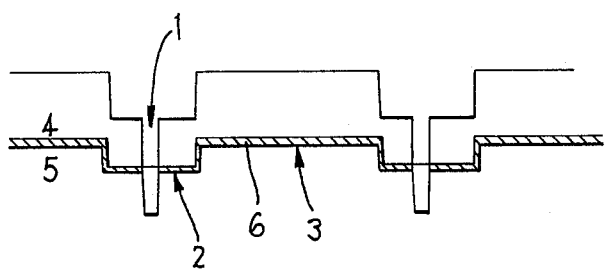
FIG. 2 is a view showing the section taken along the line A—A' and an area immediately adjacent thereto in FIG. 1.
Figure 3:
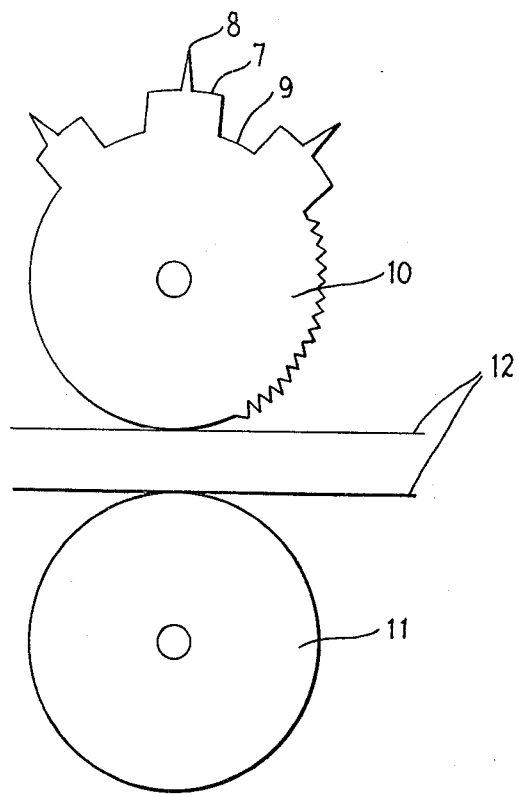
FIG. 3 is a view showing the lateral section of an embossing roll of the pressing and bonding apparatus of the present invention.
Figure 4:
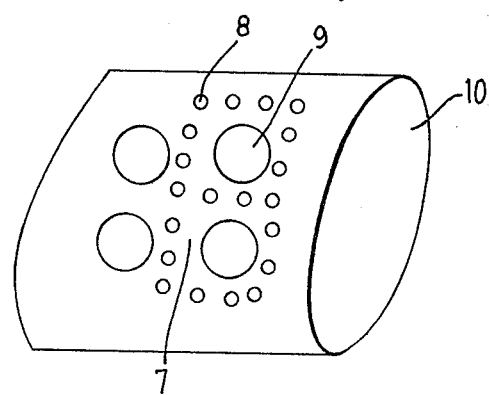
FIG. 4 is a perspective view of the embossing roll shown in FIG. 3.

SUMMARY OF REFERENCE NUMERALS:

1: strongly press-bonded areas
2: weakly press-bonded areas
3: non-press-bonded areas
4, 5, 13, 15: sheets
6, 14: polymeric absorbent
7: flat portions of embossing roll
8: convexities of embossing roll
9: concavities of embossing roll
10: embossing roll
11: receiving roll
12: laminated sheet
16: connections between non-press-bonded areas A water-absorbing sheet assembly according to the present invention is a novel highly absorbing sanitary sheet material which has an embossing pattern shown in FIGS. 1 and 2, which is imparted by pressing processing the sheet assembly with an embossing roll having an embossing surface as shown in FIGS. 3 and 4.

The convexities of an embossing roll 10 shown in FIGS. 3 and 4, that is, the highly raised embossing parts 8, correspond to parts 1 of the embossing pattern shown in FIGS. 1 and 2, and the flat portions of the embossing roll shown in FIGS. 3 and 4, the low embossing parts 7, correspond to the parts 2 of the embossing pattern shown in FIGS. 1 and 2. Furthermore, the concavities 9 on the embossing roll shown in FIGS. 3 and 4 correspond to the parts 3 of the embossing pattern shown in FIGS. 1 and 2, that is, the non-press-bonded areas. This embossed structure functions to stabilize the composite state of the resulting highly absorbing sanitary sheet material. More specifically, the parts 1 shown in FIG. 1 stabilize the composite state of the novel highly absorbing sanitary sheet material, and the influences of the embossing processing on these parts 1 are small and the crepe residual ratio is very high. Accordingly, reduction of the liquid absorbing speed and the water-absorbing property is controlled by these parts. Furthermore, in the parts 3 shown in FIG. 1, elongation of the sheets, especially the crepe paper, is remarkably reduced, and if these non-press-bonded areas are continuous to and communicated with each other as indicated by reference numeral 16 in FIG. 1, the orienting characteristic is not manifested in the crepe paper, the sheet assembly is kept soft and flexible and absorbed water is dispersed uniformly and promptly. Intermediate flat portions contiguous to the parts 3 in FIG. 1, that is, areas 2 in FIG. 1, act as zones for controlling elongation of the sheets at the parts 3.

Referring to FIG. 3, reference numeral 11 represents a receiving roll and reference numeral 12 represents a laminated sheet to be embossed and pressed.

When the embossing roll of the present invention is used, the convexities perform strong pressing of both the sheets, and since the total area of these convexities may be much smaller than the area of the flat portions, the softness and flexibility of the resulting laminated sheet are improved. The flat portions press both the sheets weakly to an appropriate degree. When the receiving roll is composed of a soft material, pressing by these flat portions is especially necessary and important. The concavities do not press the sheets at all, and in the areas corresponding to the concavities, the polymeric absorbent is kept free and sufficiently exerts the water-absorbing function. In the sheet assembly of the present invention, the area ratio of the press-bonded areas of the two sheets to the non-press-bonded areas of the two sheets is appropriately selected within the range of from 1:0.05 to 1:4. It is preferred that the convexities 1 are arranged to surround the concavities 3 as shown in FIG. 1. A pattern in which the concavities 3 are arranged at certain intervals is especially preferred, as where convexities 1 are arranged between every two concavities 3 adjacent to each other in either the longitudinal or lateral directions, and one convexity 1 is arranged between every two concavities 3 adjacent to each other in a diagonal direction. The distance between every two adjacent convexities should be about 1 to 10 mm. If the distance between convexities is too small, the softness of the resulting composite is insufficient, and when the distance is too large, the fixation of the polymeric absorbent to the sheets is insufficient.

FIG. 2 is a view showing the section taken along the line A—A' in FIG. 1. As shown by FIG. 2, the laminate sheet comprising the polymeric absorbent 6 interposed between the upper and lower sheets 4 and 5 is pressed and bonded by the flat portions 2 on the surface of the embossing roll, especially strongly by the convexities 1.

Figure 5:
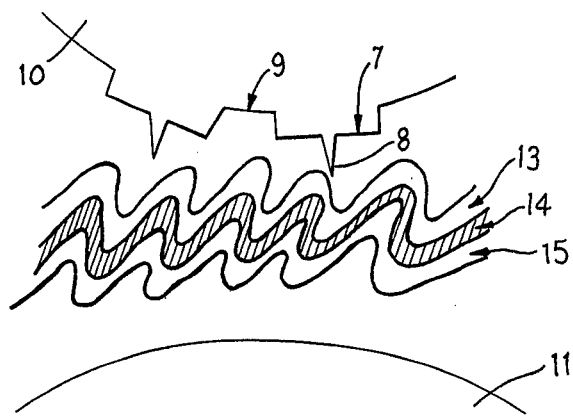
FIG. 5 is a sectional view showing a laminate sheet before the embossing treatment.
Figure 6:
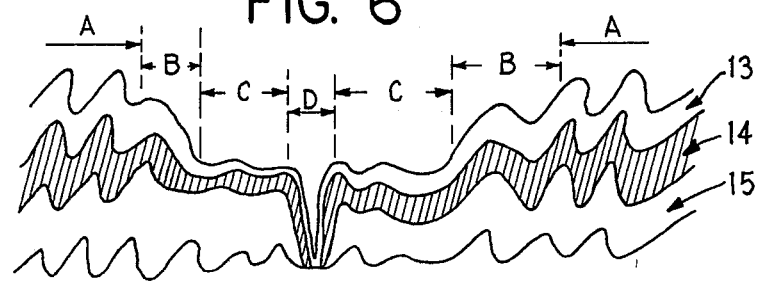
FIG. 6 is a sectional view showing the laminate sheet of FIG. 5 after the embossing treatment.

A modification of the pattern imparted to the sheet assembly by the embossing treatment using the pressing and bonding apparatus comprising the embossing roll of the present invention as shown in FIGS. 3 and 4 is illustrated in FIGS. 5 and 6. A laminate sheet comprises two upper and lower sheets 13 and 15 and a polymeric absorbent 14 interposed therebetween. Before the embossing treatment, as shown in FIG. 5, the laminate sheet is placed between an embossing roll 10 and a receiving roll 11 as shown in FIG. 5. When the laminate sheet is subjected to the embossing treatment, the laminate sheet is embossed and pressed as shown in FIG. 6. In FIG. 6, the areas C and D correspond to the parts processed by low embossing parts 7 and high embossing parts 8, respectively, and the areas D are especially deeply embossed by the high embossing parts 8 so as to perform stabilization of the shape and dimensions of the highly absorbing sanitary sheet material of the present invention very effectively. In order to prevent reduction of the crepe ratio of the water-absorbing paper owing to excessive elongation by such deep embossing, the low embossing parts 7 are formed on the surface of the embossing roll and the weakly embossed areas C are formed. By virtue of the presence of the areas C, the deformation of the water-absorbing paper in the areas A corresponding to the concavities 9 on the surface of the embossing roll is reduced. Accordingly, in the highly absorbing sanitary sheet material having the embossed structure as shown in FIG. 6, the areas D are most strongly pressed and bonded and the areas C are lightly pressed and bonded, and in these areas, the liquid-absorbing property is recuded by the embossing treatment. On the other hand, the areas A in FIG. 6 are hardly influenced by the embossing treatment, and therefore, in these areas A, the crepe retention ratio is high and the liquid-absorbing property of the upper paper is hardly reduced. Moreover, in these areas A, a slight clearance is retained between the upper paper 13 and the polymeric absorbent 14, and water permeating through the upper paper 13 is stored in this clearance and the time of contact with the polymeric absorbent is prolonged and the liquid-absorbing property can be fully exerted.

Figure 7:
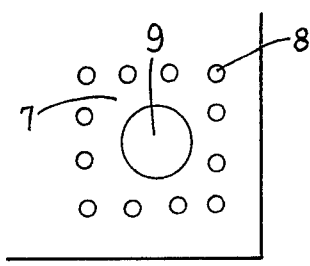
FIG. 7 is a plan view diagrammatically illustrating an embossing pattern of an embossing roll used in the Examples.

The present invention will now be described in detail with reference to the following Examples. In these Examples, an embossing roll (composed of stainless steel S-25C) was used having convexities 8 and concavities 9 arranged on the surface thereof as shown in FIG. 7. The area of the flat portions 7 was determined so that a desired embossing area ratio would be obtained. The diameter of the embossing roll was 100 mm, and the height of the convexities 8 was 0.4 mm (in Examples 1 and 2) or 0.8 mm (in Examples 3 and 4). The distance between every two adjacent convexities 8 was ¾ mm, the diameter of the concavities 9 was 2.6 mm, and the depth of the concavities was 1.6 mm. A roll composed of Teflon (hardness of 80°) with a diameter of 100 mm was used as the receiving roll.

EXAMPLE 1

Between absorbing papers, each having a base weight of 25 g/m$^2$, a powder of self-crosslinked sodium polyacrylate (having a particle size smaller than 450$\mu$) was interposed at a base weight of 20 g/m$^2$. The assembly was embossed at an embossing temperature of 160° C under an embossing pressure of 5 Kg/cm, while the embossing area ratio (press-bonded areas/non-press-bonded areas) was adjusted to 4.1, thereby to fix the polymeric absorbent and obtain a highly absorbing sheet material.

EXAMPLE 2

Between an absorbing paper and a water-proof paper, each having a base weight of 25 g/m$^2$, a powder of crosslinked carboxymethyl cellulose (having a particle size smaller than 450$\mu$) was interposed at a base weight of 30 g/m$^2$. The assembly was embossed at an embossing temperature of 160° C under an embossing pressure of 8 Kg/cm, while the embossing area ratio was adjusted to 8.0, thereby to fix the polymeric absorbent and obtain a highly absorbng sheet material.

EXAMPLE 3

Between a rayon paper (20% rayon incorporated) and a polyethylene sheet, each having a base weight of 30 gm/m$^2$, a powder of a starch-polyacrylic acid graft copolymer (having a particle size smaller than 450$\mu$) was interposed at a base weight of 20 g/m$^2$. The assembly was embossed at an embossing temperature of 140° C under an embossing pressure of 10 Kg/cm, while the embossing area ratio was adjusted to 10.5, thereby to fix the polymeric absorbent and obtain a highly absorbing sheet material.

EXAMPLE 4

Between an absorbing paper and a polyethylene-laminated paper, each having a base weight of 30 g/m$^2$, a powder of self-crosslinked sodium polyacrylate (having a particle size smaller than 450$\mu$), was interposed at a base weight of 30 g/m$^2$. The assembly was embossed at an embossing temperature of 120° C. under an embossing pressure of 8 Kg/cm, while the embossing area ratio was adjusted to 5.5, thereby to fix the polymeric absorbent and obtain a highly absorbing sheet material.

Each of the highly absorbing sheet obtained in Examples 1 through 4 excellent in the softness and flexibility and had a good absorbing property.

What is claimed is:

1. A laminated, water-absorbing, sheet assembly comprising two sheets and a layer of polymeric absorbent powder interposed between said two sheets, at least one of said sheets being a water-permeable, creped sheet, said sheet assembly being embossed in a pattern such that said sheet assembly consists essentially of first areas in which said sheets are deeply embossed and strongly press-bonded to each other, second areas in which said sheets are shallowly embossed and weakly press-bonded to each other and third areas in which said sheets are not embossed and not press-bonded to each other, said third areas being continuous to and communicating with each other, and the area ratio of press-bonded areas of said sheets to non-press-bonded areas of said sheets being in the range of from 1:0.05 to 1:4.

2. A water-absorbing sheet assembly as set forth in claim 1, wherein both of said two sheets are water-permeable sheets.

3. A water-absorbing sheet assembly as set forth in claim 1, wherein one of said two sheets is a water-permeable sheet and the other sheet is a water-impermeable sheet.

4. A water-absorbing sheet assembly as set forth in claims 1, wherein the polymeric absorbent is a self-crosslinked polyacrylic acid salt.

5. A laminated, water-absorbing, sheet assembly comprising two sheets, at least one of which is a water-permeable crepe paper sheet; a layer of polymeric absorbent powder interposed between said two sheets, said one sheet and said layer of polymeric absorbent powder being embossed with a recurring pattern of embossing relative to the other sheet, said other sheet being substantially flat, said pattern of embossing providing (1) first, spaced-apart, relatively thick zones in which said one sheet and said layer of polymeric absorbent powder are not embossed and extend generally parallel with said other sheet, said first zones being continuous to and communicating with each other, (2) second zones which are spaced from each other and from said first zones and which are located between said first zones, said one sheet and said layer of polymeric absorbent powder being deeply embossed toward said other sheet at said second zones, and (3) third zones completely occupying the spaces between said first and second zones, said one sheet and said layer of polymeric absorbent powder being shallowly embossed toward said other sheet in said third zones, the thickness of said third zones being less than the thickness of said first zones and greater than the thickness of said second zones, the ratio of the sum of the areas of said second and third zones to the sum of the areas of said first zones being in the range of from 1:0.05 to 1:4.

* * * * *